US007824412B2

(12) United States Patent
Falahee

(10) Patent No.: US 7,824,412 B2
(45) Date of Patent: Nov. 2, 2010

(54) CEMENT/BIOLOGICS INSERTER AND METHOD FOR BONE-FASTENER FIXATION AUGMENTATION

(75) Inventor: Mark H. Falahee, Ann Arbor, MI (US)

(73) Assignee: Medical Design Instruments LLC, Ann Arbor, MI (US)

( * ) Notice: Subject to any disclaimer, the term of this patent is extended or adjusted under 35 U.S.C. 154(b) by 1439 days.

(21) Appl. No.: 10/935,609

(22) Filed: Sep. 7, 2004

(65) Prior Publication Data

US 2005/0055030 A1    Mar. 10, 2005

Related U.S. Application Data

(60) Provisional application No. 60/500,630, filed on Sep. 5, 2003.

(51) Int. Cl.
    *A61B 17/56* (2006.01)
(52) U.S. Cl. .................................................. 606/92
(58) Field of Classification Search ............. 606/92–94
    See application file for complete search history.

(56) References Cited

U.S. PATENT DOCUMENTS

| 4,399,814 A * | 8/1983 | Pratt et al. ........................ 606/94 |
| 4,653,489 A * | 3/1987 | Tronzo ........................ 606/65 |
| 5,346,495 A * | 9/1994 | Vargas, III .................... 606/92 |
| 6,048,343 A * | 4/2000 | Mathis et al. ................. 606/72 |
| 6,679,890 B2 * | 1/2004 | Margulies et al. ............. 606/94 |
| 7,048,743 B2 * | 5/2006 | Miller et al. .................. 606/94 |
| 2003/0105468 A1 * | 6/2003 | Gorek .......................... 606/92 |

* cited by examiner

*Primary Examiner*—Eduardo C Robert
*Assistant Examiner*—David Comstock
(74) *Attorney, Agent, or Firm*—Gifford, Krass, Sprinkle, Anderson & Citkowski, P.C.

(57) ABSTRACT

An inserter and associated method improve the placement of a fastener into a bone. Although ideally suited to the placement of a pedicle screw into a vertebral body (VB), the apparatus and method are applicable to other bones and fasteners, pins, and the like. The apparatus includes cannulated body having a proximal end, a distal end, and a threaded section therebetween. The proximal end is shaped for rotational tightening by a wrench or other tool, and the distal end including a perforated nozzle so that cement and/or biologics may be injected into the bone through the cannulated body. The proximal end includes a Lur-loc or other appropriate fitting to receive a cement-filled syringe. The device is also preferably disposable using, for example, clear plastic construction. The inserter may further including a member for sealing the nozzle relative to a bone. Such a member may be composed of a silatstic or other compressible material, or may be inflatable. At least the distal end of the device is preferably provided with varying diameters for different insertion sizes.

10 Claims, 3 Drawing Sheets

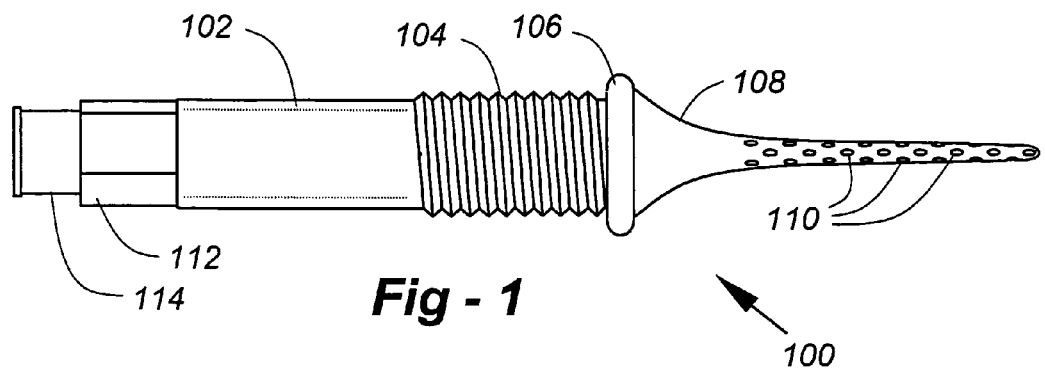
Fig - 1
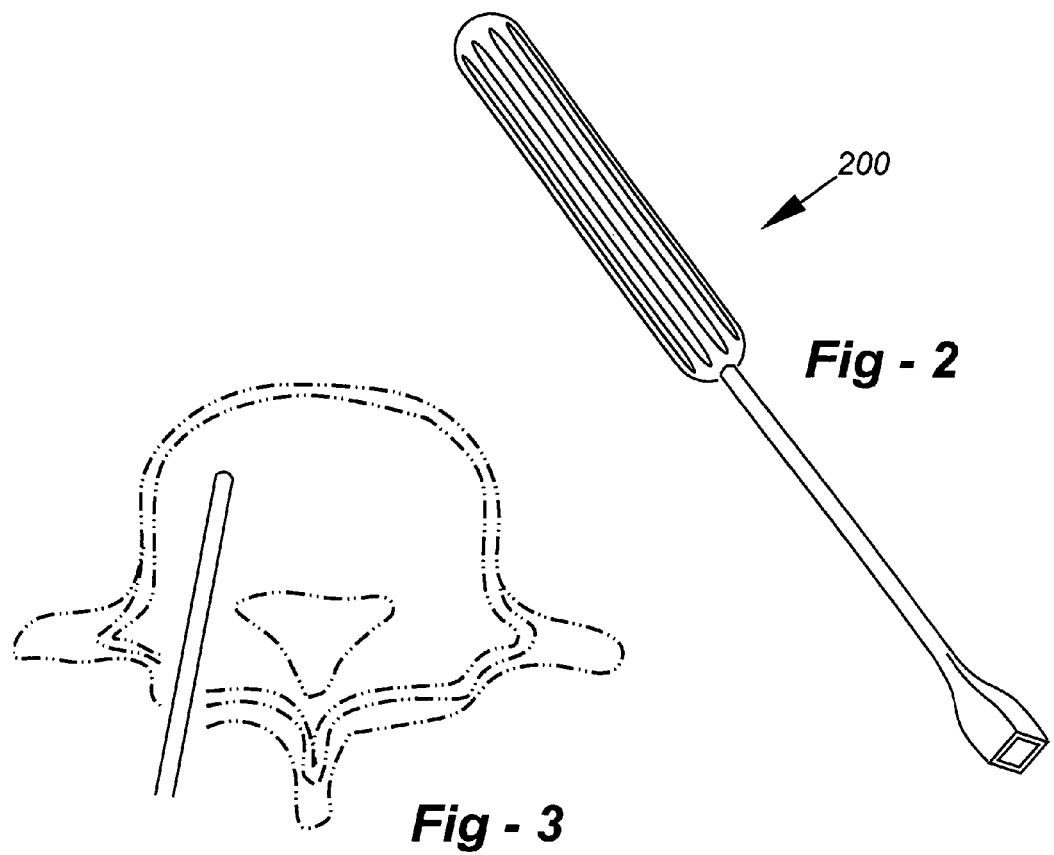
Fig - 2
Fig - 3

CEMENT/BIOLOGICS INSERTER AND METHOD FOR BONE-FASTENER FIXATION AUGMENTATION

REFERENCE TO RELATED APPLICATION

This application claims priority from U.S. Provisional Patent Application Ser. No. 60/500,630, filed Sep. 5, 2003, the entire content of which is incorporated herein by reference.

FIELD OF THE INVENTION

This invention relates generally to spinal surgery and, in particular, to methods and apparatus associated with the delivery of cement or biological materials to augment the strength of the vertebral body in osteoporotic or otherwise weakened bone conditions, in preparation for pedicle fixation.

BACKGROUND OF THE INVENTION

Pedicle fixation into osteoporotic spine is tentative fixation at best, often leading to rapid, post operative loosening. Cement injection into the vertebral body (VB) has been utilized for osteoporotic compression fractures (vertebroplasty, kyphoplasty). Injection for augmentation of pedicle fixation is also done, utilizing the tapped pedicle screw hole as an access point.

Currently, however, there is no specific tool or safe system of injection/pressurization. Surgeons often use a cement-filled syringe with a large bore needle, or no needle at all. As such, cement cannot be placed under pressure into vertebral body utilizing a needle or syringe, thus affording minimal VB augmentation. Back flow risks cement flowing into the vertebral neural canal if the pedicle is medially violated. Retrograde flow out of the pedicle entry point may lead to spillage and cleanup problems.

With this background, there remains a need for delivery of cement or biological materials to augment the strength of the vertebral body in osteoporotic or otherwise weakened bone conditions, in preparation for pedicle fixation.

SUMMARY OF THE INVENTION

This invention resides in an inserter and associated method for improving the placement of a fastener into a bone. Although ideally suited to the placement of a pedicle screw into a vertebral body (VB), the apparatus and method are applicable to other bones and fasteners, pins, and the like.

In terms of apparatus, a preferred device according to the invention includes a cannulated body having a proximal end, a distal end, and a threaded section therebetween. The proximal end is shaped for rotational tightening by a wrench or other tool, and the distal end including a perforated nozzle. With such an arrangement, the distal end may be inserted into a bone and tightened at the proximal end so that cement and/or biologics may be injected into the bone through the cannulated body.

In the preferred embodiment, the proximal end includes a Lur-loc or other appropriate fitting to receive a cement-filled syringe. The device is also preferably disposable using, for example, clear plastic construction. The inserter may further including a member for sealing the nozzle relative to a bone. Such a member may be composed of a silatstic or other compressible material, or may be inflatable. At least the distal end of the device is preferably provided with varying diameters for different insertion sizes.

A method of fortifying a bone according to the invention to receive a fastener comprises the steps of drilling and tapping a hole in the bone. The inserter apparatus is advanced into the tapped hole, preferably through rotation. The process continues with injecting cement into the hole through the fastener, removing the inserter, and installing the fastener. According to the preferred protocol, the step of injecting cement into the hole through the fastener includes attaching a cement-filled syringe to the injector and depressing the syringe.

BRIEF DESCRIPTION OF THE DRAWINGS

FIG. 1 is a side-view drawing of a preferred cement injector according to the invention;

FIG. 2 is a perspective drawing of a geometric wrench according to the invention;

FIG. 3 is a drawing of a pedicle being probed to receive an inventive cement injector;

DETAILED DESCRIPTION OF THE INVENTION

Figure 4:
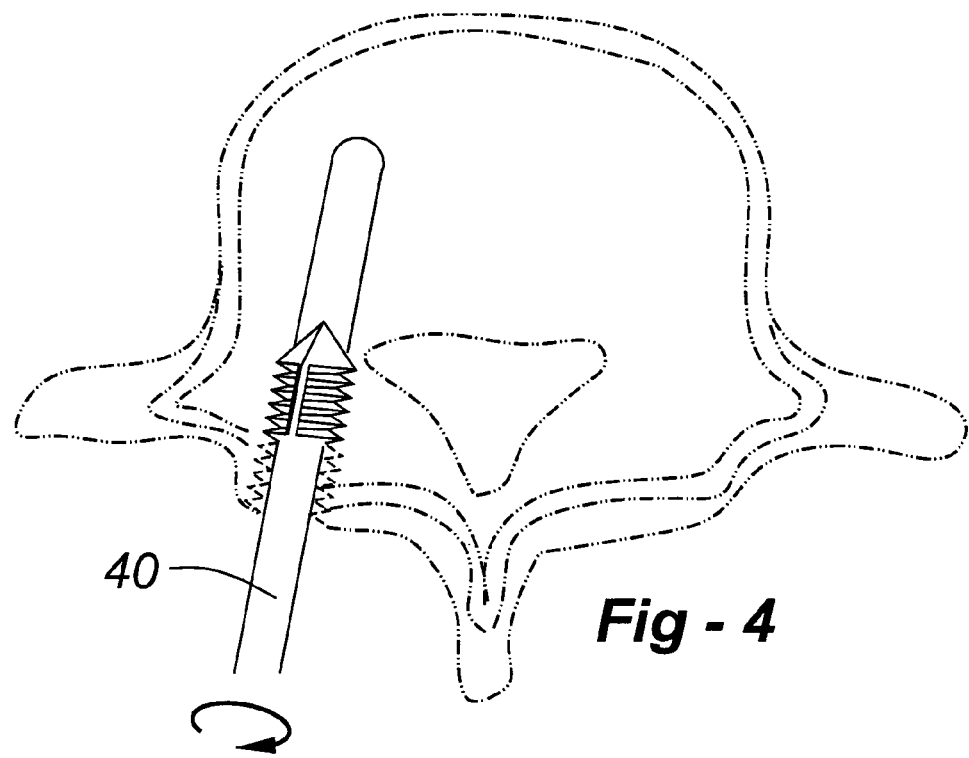
FIG. 4 is a drawing showing the pedicle hold being tapped per usual technique.

FIG. 1 is a side-view drawing of a preferred embodiment of the invention. The device, indicated generally at 100, preferably comprises a disposable, clear plastic body 102, including a tapered tip 108 with perforations 100, the diameter of the tip 108 being smaller than that of the hole tapped for the pedicle access point. The device 100 further includes a threaded section 104, and an optional plastic ring, plug or inflatable ring 106 to minimize or prevent backflow. A square- or other geometrically-shaped proximal base 112 is provided to accept the wrench 200 shown in FIG. 2, and a Lur-lock base 114 is provided for syringe hook-up.

According to the invention, varying diameters will be available, each with a threaded waist matching a current commercial tap size, such as 4.5, 5.0, 5.5, and so forth, to engage and seal against the tapped pedicle channel. The tapered end 108 preferably includes a slight taper of smooth plastic, which functions as a guide for centralization, thereby more effectively plugging the pedicle/vertebral body interface. Radiopaque may be provided at the tip, the front of the plug, or elsewhere, to assist with radiological identification.

Surgical Technique

FIGS. 3-7 illustrate a surgical technique performed in accordance with this invention. In FIG. 3, the site is identified, and the pedicle hole probed per, as shown in FIG. 3. The hole is tapped, as shown in FIG. 4, utilizing commercially available tap 40, and appropriately sized cement inserter 100 is selected to correspond to the tapped bore.

Figure 5:
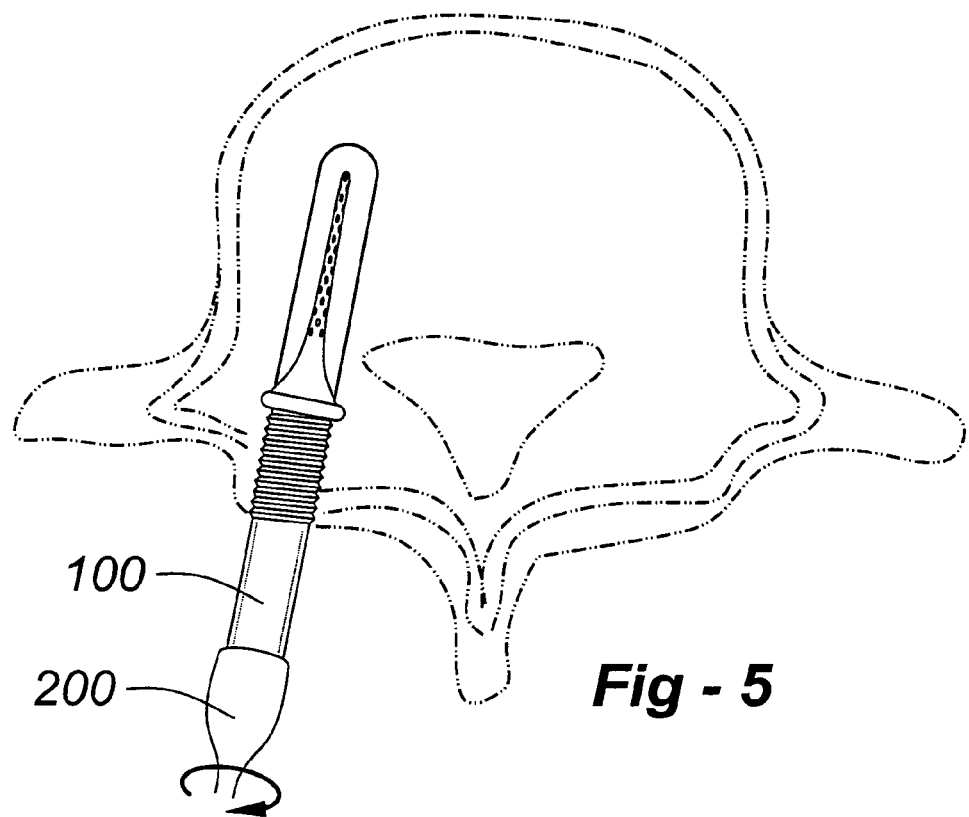
FIG. 5 is a drawing which shows the cement applicator being inserted utilizing the wrench of FIG. 2.
Figure 6:
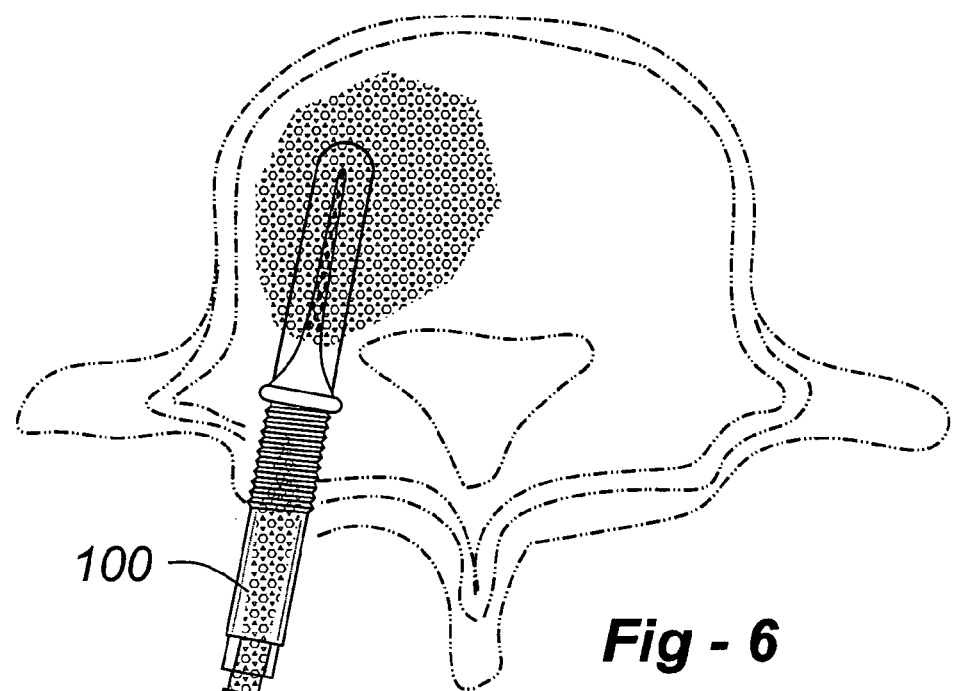
FIG. 6 is a drawing which shows cement being injected.

As shown in FIG. 5, a cement inserter is screwed into place utilizing wrench 200, preferably until no threads are visible. The depth and location of the device may be checked utilizing C-arm AP/LAT visualization, if an inflatable ring is provided, the ring is inflated at this time. The wrench is removed, and a cement-filled syringe 60 is attached to the Lur-lock fitting, as shown in FIG. 6, and cement pressurization takes place.

Again, C-arm techniques may be utilized to check the cement plume developing within the vertebral body, as it extends out from the pedicle hole.

Figure 7:
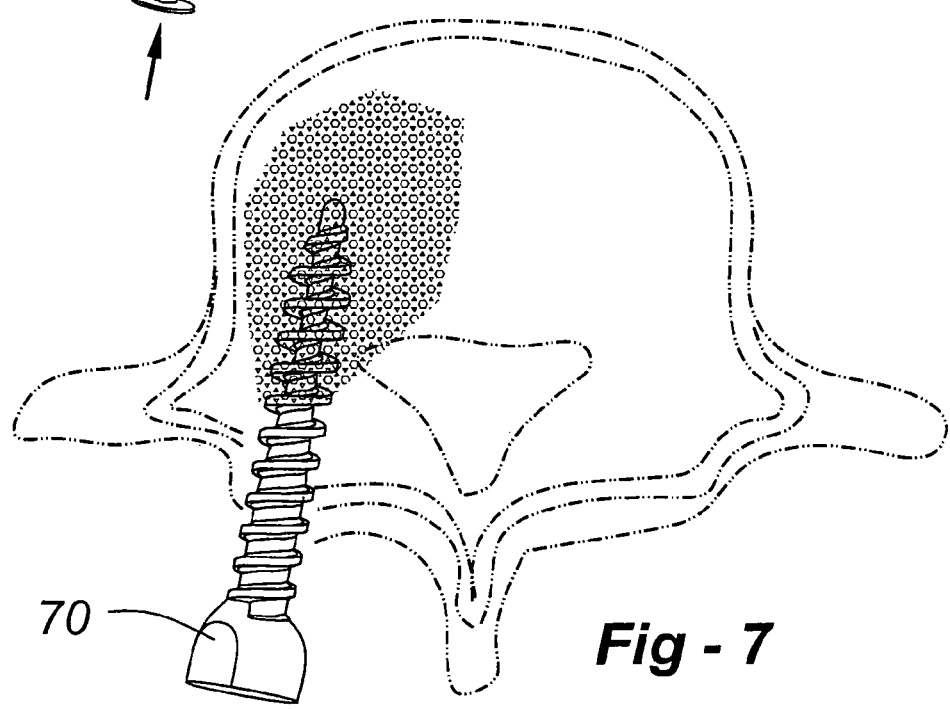
FIG. 7 is a drawing which shows a pedicle screw being inserted into a cement bed.

When sufficient cement has been inserted, typically on the order of 2 cc's, the viscosity of excess cement may be checked on field, with the cement introducer 100 being removed when thickening initiates. As shown in FIG. 7, a pedicle screw 70 has been inserted per standard procedures. The process may be repeated, on the other side of the vertebral body, or at one or more different levels, as necessary.

I claim:

1. An inserter for improving the placement of a fastener into a bone, comprising:
   a cannulated body having a proximal end, a distal end, and a threaded section therebetween;
   the proximal end having a square or other geometrical cross-section for rotational tightening by a wrench;
   the distal end including a smooth, tapered perforated nozzle;
   a circumferential member around the body for sealing the nozzle relative to a bone; and
   whereby the distal end may be inserted into a bone and tightened at the proximal end so that cement and/or biologics may be injected into a region of the bone through the cannulated body, with the body then being removed to receive a fastener into the region of injected cement.

2. The inserter of claim 1, wherein the proximal end includes a fitting to receive a cement-filled syringe.

3. The inserter of claim 1, wherein the body is disposable after use.

4. The inserter of claim 1, wherein the body is composed of clear plastic.

5. The inserter of claim 1, wherein the member is compressible.

6. The inserter of claim 1, wherein the member is inflatable.

7. The inserter of claim 1, including a plurality of distal ends with varying diameters for different insertion sizes.

8. A method of fortifying bone to receive a fastener, comprising the steps of:
   drilling a hole in the bone;
   tapping the hole;
   providing the inserter of claim 1;
   advancing the inserter into the tapped hole through rotation;
   injecting cement into the hole through the fastener;
   removing the inserter; and
   installing the fastener.

9. The method of claim 8, wherein the step of injecting cement into the hole through the fastener includes attaching a cement-filled syringe to the injector and depressing the syringe.

10. The method of claim 8, wherein:
    the bone is a vertebral body; and
    the fastener is a pedicle screw.

* * * * *